United States Patent [19]

Harewood

[11] Patent Number: 5,744,321
[45] Date of Patent: Apr. 28, 1998

[54] DETECTION OF FISH SPOILAGE BY COLORIMETRY

[75] Inventor: Patrick Harewood, N. Branford, Conn.

[73] Assignee: GEM Biomedical, Inc., Hamden, Conn.

[21] Appl. No.: 803,946

[22] Filed: Feb. 21, 1997

[51] Int. Cl.$^6$ .............. C12Q 1/04; C12Q 1/00; C12Q 1/02

[52] U.S. Cl. .............. 435/34; 435/4; 435/29; 435/30; 435/31; 435/32; 435/39; 435/874; 435/875; 435/876; 435/877

[58] Field of Search .............. 435/34, 4, 29, 435/30, 31, 32, 39, 874, 875, 876, 877

[56] References Cited

U.S. PATENT DOCUMENTS 5,053,339  10/1991  Patel .............. 435/34
5,411,666  5/1995  Hollis et al. .............. 435/34
5,643,571  7/1997  Sin et al. .............. 435/34

OTHER PUBLICATIONS

"The Use of Tetrazolium Sals For Assessing The Quality of Iced White Fish", Shewan et al., J. Sci. Food Agric., vol. 3, pp. 222 to 226, (Apr. 1957).

*Primary Examiner*—Louise Leary

[57] ABSTRACT

A rapid, on-site method for indicating the degree of spoilage, if any, of finfish by the level of bacteria present therein. A small quantity of flesh is cut from a representative fish and kneaded in a bacterial nutrient broth to extract any bacteria present. A triphenyl tetrazolium dye is added as an indicator reagent, followed by an anionic surfactant and a lower alkyl alcohol. The developed color, if any, is compared to a control color chart representative of acceptable and unsatisfactory degrees of bacterial contamination or spoilage.

13 Claims, 4 Drawing Sheets

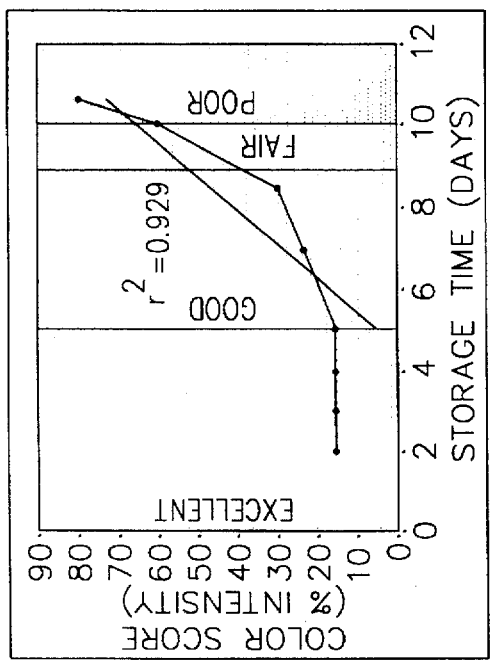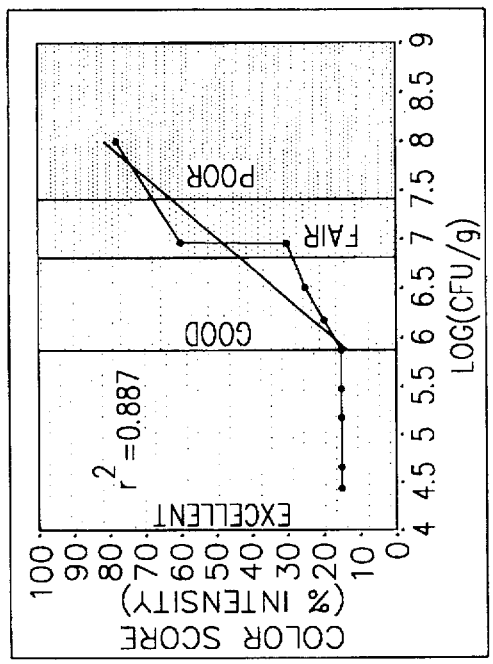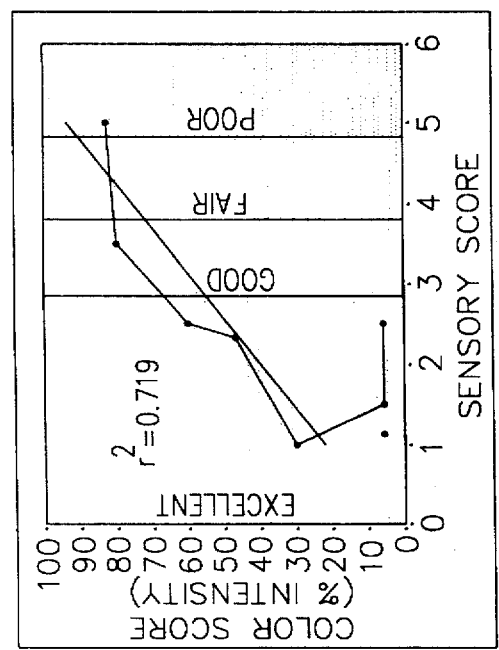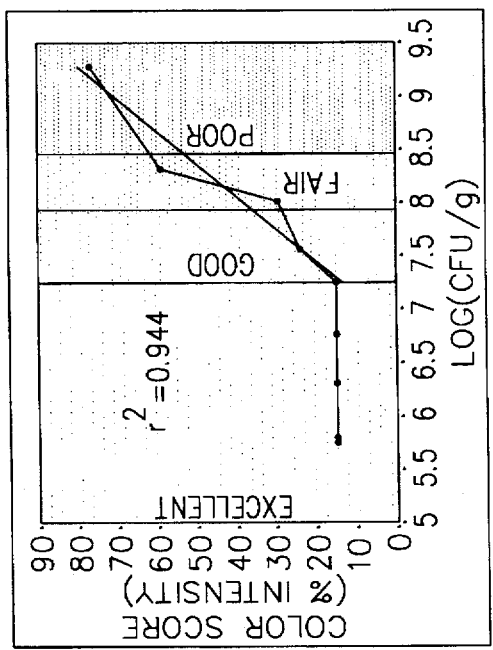

DETECTION OF FISH SPOILAGE BY COLORIMETRY

BACKGROUND OF THE INVENTION

1. Field of the Invention

The present invention relates to the detection and evaluation of the extent of degradation or spoilage of finfish tissue caused by bacteria such as pseudomonas putrefaciens, as an indication of the degree of quality of the fish.

The bacterial degradation of fish begins when a fish dies. Bacterial spoilage initially affects the texture and taste of fish and, with time, bacterial growth progresses to the extent that the fish is no longer fit for consumption.

The flesh of living fish is usually free of bacteria, but the normal barriers that protect fish muscle and tissue from invasion from bacteria begin to break down when the fish dies. Thus, if the fish is not fresh, spoilage progresses rapidly to produce a number of metabolic reaction products and odors that vary depending on temperature and age.

From a commercial standpoint it is important for purchasers of large volumes of fish, such as wholesalers and retailers, to be assured of the freshness and quality of finfish being purchased from fishing boats or fleets in relation to the price being asked.

2. Description of the State of the Art

Traditional methods for evaluating the freshness or degree of spoilage of fish include sensory evaluation (appearance, feel and smell), trimethylamine determination and bacterial population determination (total plate counts).

These methods are of only limited use because they are subjective, debatable, require highly trained or skilled personnel and/or specialized equipment, or are too expensive or time consuming for the routine analysis of large numbers of fish. It is highly desirable to be able to evaluate fish quality in-situ, i.e., directly at the retail outlet, and to be able to make an objective evaluation within minutes. The retail outlet is the place where there will be a high degree of spoilage, and where color will most frequently be detected.

SUMMARY OF THE INVENTION

The present invention involves a novel colorimetric method for rapidly evaluating the degree of bacterial degradation, if any, (spoilage) of finfish, such as codfish, catfish and winter flounder, for example, by mixing the fish flesh with a bacterial nutrient broth, and reacting the extract with a water-soluble chromogen such as an ionized tetrazolium dye salt which undergoes a reduction reaction with the fish bacteria to produce a water-insoluble formazan dye or colored reaction product. Next a surface active agent is added, to help solubilize the formed formazan dye, to produce lysis and stop the reaction, and an aliphatic alcohol solvent is added to dissolve the formed formazan dye or colored reaction product, and prevent further breakdown and darkening with time. The dissolved reaction product has a color which is intensified depending upon the bacterial population of the fish sample and which can be evaluated colorimetrically by visual comparison with a standard color chart indicative of low, medium and high bacterial populations, which I refer to under the trademark Fish-CHECK Color Chart.

THE DRAWINGS

FIGS. 1 to 5 are comparative graphs illustrating the relationship between storage time, aerobic plate count, *Pseudomonas putrefaciens* count, trimethylamine count and sensory score, respectively, and the % intensity of color developed in the sample broth solutions produced from codfish according to the novel method of the present invention, as measured against the colors of a conventional Pantone® Professional Color System intensity chart such as Pantone® Color Specifier 747XR;

FIGS. 6 to 9 are comparative graphs, corresponding to those of FIGS. 1 to 3 and 5, and pertaining to sample broth solutions produced from catfish according to the novel method of the present invention, and FIGS. 10 to 14 are comparative graphs corresponding to those of FIGS. 1 to 5 and pertaining to sample broth solutions produced from winter flounder according to the present invention.

DETAILED DESCRIPTION

Figure 1:
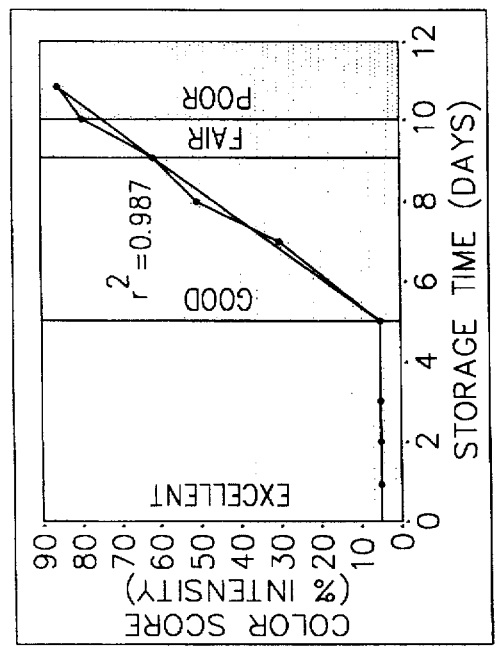

The novel method of the present invention is one which can be carried out quickly by any lay person, with minimum training, and with portable supplies which can be carried on one's person. The method can be carried out in-situ in any environment, such as on a fishing boat, without interference from the odor of the environment. Also, the test results are objective and visually demonstrated by a color comparison which is clear to any lay person without the need for special training or evaluation equipment. In the case of dark-flesh finfish, such as tuna fish, additional reactants such an oxidizing or bleaching agent, preferably hydrogen peroxide, and a defoamer are added to bleach the muscle pigments and lighten the color of the solution so that any color that appears during the assay is due to the reduction of the tetrazolium dye.

The novel, simplified colorimetric test process of the present invention is based upon the discovery that triphenyl tetrazolium dye salts are colorless, ionized, water soluble and capable of passing through the cell wall into a bacterial cell while undergoing a reduction reaction to form a non-ionic, water-insoluble, red-colored triphenyl tetrazolium formazan compound which is deposited within the bacterial cells. The intensity of the formed color is proportional to the concentration of the bacteria present, necessary to produce the reduction reaction, and therefore the visible color intensity provides a measure of the bacteria concentration which, in turn, provides an indication of the quality of the fish being tested.

The present process is conducted on finfish fillets which are believed to be fresh and/or which have been kept on ice. A predetermined weight of a fish fillet, such as 25 gms, is kneaded with a predetermined volume of a liquid growth medium, such as 25 ml, (1:1 ratio) for 2 to 5 minutes at room temperature, e.g., 23° to 25° C., shaking vigorously, and then a predetermined volume of the liquid filtrate, such as 5 ml, is mixed with a small amount, such as 1 ml, of the colorless triphenyl tetrazolium dye salt indicator reagent and allowed to incubate for 10 to 20 minutes at room temperature, e.g., 15°–25° C., shaking vigorously every 5 minutes. The following reaction takes place with the use of 2,3,5-triphenyl tetrazolium chloride as the indicator reagent:

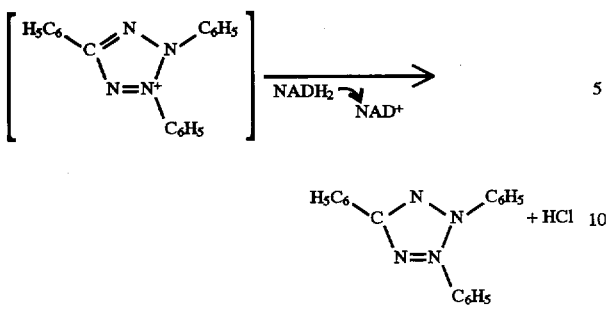

This reduction reaction is enabled by the functioning electron transport system of the viable bacterial flora on the fish and proceeds in proportion to the quantity of the enabling bacteria present. The greater the concentration of the red-colored 2,3,5-triphenyl tetrazolium formazan formed in the bacterial cells, the greater the intensity of the color of the formazan solution extracted from the sample.

Additional essential process steps involve (a) the addition of a small amount, e.g., 2 or 3 ml, of a surface active agent, preferably an anionic long chain alkyl sulfate salt such as sodium dodecyl sulfate, to the sample, immediately after incubation. This stops the reduction reaction producing lysis of the bacterial cells, releasing and solubilizing the formazan, and denaturing the fish protein into a metaprotein to form a clear solution, and (b) the addition of a small amount, e.g., 1 ml, of a short chain aliphatic alcohol, such as methanol, to stabilize the color of the clear formazan solution, apparently by destroying any residual enzyme activity.

The intensity of the color of the solution is compared by a visual colorimetric comparison with control color strips representative of known concentrations of formazan solution ranging from substantially-colorless, for a product of excellent quality, light reddish color representing good quality, darker red color representing borderline quality, and intense red color representing unacceptable quality. These control colors are preliminarily determined by known traditional methods used to measure the bacterial content of finfish of excellent, good, borderline and unacceptable freshness, such as total plate count determination, trimethylamine (TMA) determination, and sensory (odor) determination. Such traditional methods are reliable but are limited in that they require specialized analytical laboratory equipment and/or highly trained personnel, and are either too expensive or time-consuming for the routine analysis of fish. More importantly, most of these traditional methods are not practical or possible in-situ on a fishing boat or at dockside.

In the case of finfish having dark-colored flesh, such as tuna fish, which contain red pigment in the muscle flesh, a final step must be applied, prior to the color comparison of the solution with the control color strips. This involves the addition of a small amount of a bleaching or decoloring agent such as hydrogen peroxide ($H_2O_2$) and a defoaming agent, such as a dilute silicone emulsion, which is added to dissipate the considerable foam which is generated by the release of oxygen during the bleaching reaction. This step may be integrated with step (b) whereby the surface active agent is added to the sample immediately after incubation and allowed to stand for another 15 minutes. Then the aliphatic alcohol, the bleaching agent and the defoamer must be added to the solution in successive order, with the solution being shaken between each addition, to bleach the colored pigments present in the tuna muscle so that any color developed during the assay is caused by the reduction of the tetrazolium dye.

The following specific example illustrates the application of the present methods to the evaluation of the quality or the bacterial content of fillets from finfish of various species. The fish fillets were purchased from a local seafood retail outlet about 48 hours after harvest, immediately placed on flaked ice in insulated containers and transported to a laboratory for testing.

EXAMPLE 1

Samples of codfish (*Gadus morhua*), catfish (*Ictalcuru spp*), or winter flounder (*Pseudopleuronectes americanus*), each 25 gm in weight, were massaged by hand with 25 ml of bacterial nutrient broth (1:1 ratio) in a sterile 6"×7" strainer bag until finely divided. 5 ml of filtrate or extract from the bag were mixed with 1 ml of indicator dye reagent (2,3,5-triphenyl tetrazolium chloride) in a sterile culture tube. The tube was allowed to stand for 15 minutes at room temperature and shaken by hand vigorously at 5 minute intervals. 2 ml (3 ml for catfish) of Reagent A (10% aqueous sodium dodecyl sulfate-surface active agent) were added to the tube to stop the reaction, followed by 1 ml of Reagent B (methanol-color stabilizer). The color developed in the tube was determined using the Pantone® Professional Color Chart, in which each color is given a numerical percentage value depending upon its intensity.

Samples in two broths were evaluated, "GNA" and "GNP". "GNA" is formulated according to DIFCO protocol for Plate Count Agar (DIFCO Manual, Tenth Edition). "GNP" is a non-protein broth, a mixture of two salts adjusted to pH7, does not need autoclaving and has added stability, and hence, increased shelf life. These two features are very important in terms of manipulation. The % color intensity readings obtained using the present method were plotted against readings obtained using the other traditional methods of analysis. The degree of correlation between the traditional methods and the present method was calculated using regression analysis. High R/2 values mean that the present method correlates favorably with the other traditional method.

A microbiological determination was made using samples from the 1:1 diluted filtrate in each strainer bag which were serially diluted in 0.1% peptone and subjected to microbiological analysis. Total aerobic plate counts were conducted on standard plate count agar incubated at 25° C. for 48 hours before counting. *Pseudomonas putrefaciens* plate counts were conducted on peptone iron agar incubated at 25° C. for 48 hours. APC and *Pseudomonas putrefaciens* values were expressed as mean log CFU/g of 10 fillets per sampling day.

A trimethylamine determination was made using samples of fish tissue which were subjected to trimethylamine determination (TMA) using a modification of the procedure of Dyer published in the Journal Fish. Res. Bd Canada, Vol. 6, pp 351–358 (1945).

At each period when samples of fish fillets were removed for microbiological and chemical analyses, a sample of fillet was placed in a plastic bag, vacuum packed, and stored at −20° C. until the end of the study. The vacuum packed fillets were then packed in dry ice and sent overnight to the National Sensory Branch of the National Marine Fisheries Service, Inspection Division, Parker Street, Gloucester, Mass., for sensory analysis.

Samples were subjected to sensory evaluation by trained panelists using a "1" to "10" unstructured line scale, with "1" representing highest quality and "10" the lowest quality.

These judges were trained to determine the quality factors of seafood and seafood products based on appearance, texture and odor. Any quality factor(s) indicative of taint or decomposition, regardless of the amount of sample affected, resulted in the sample being failed, i.e., score >5. To fail a sample, the quality factors had to be both persistent and distinct.

Figure 2:
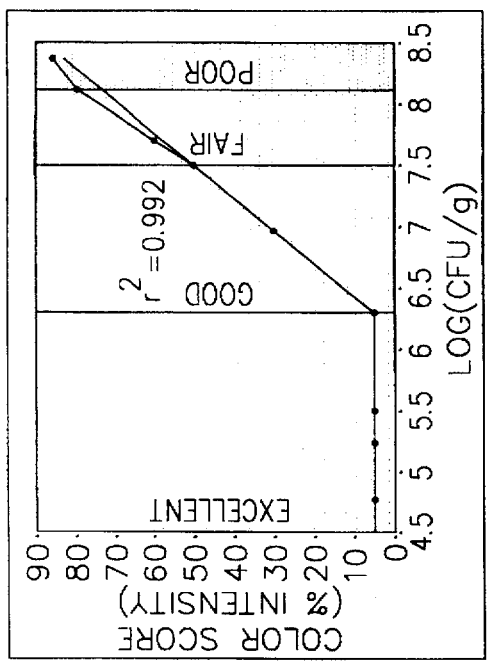
Figure 3:
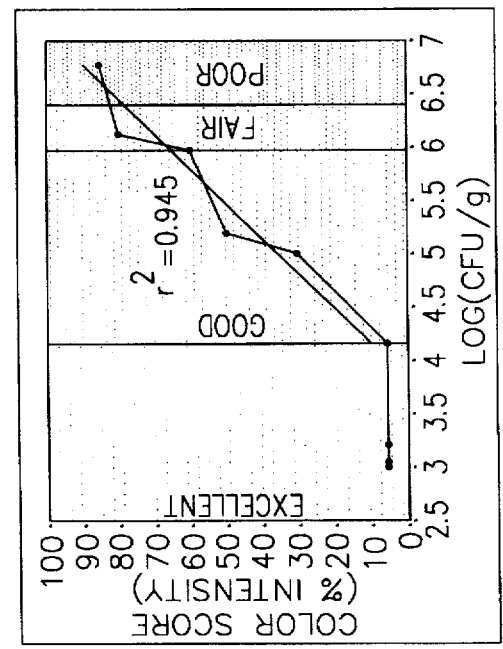
Figure 4:
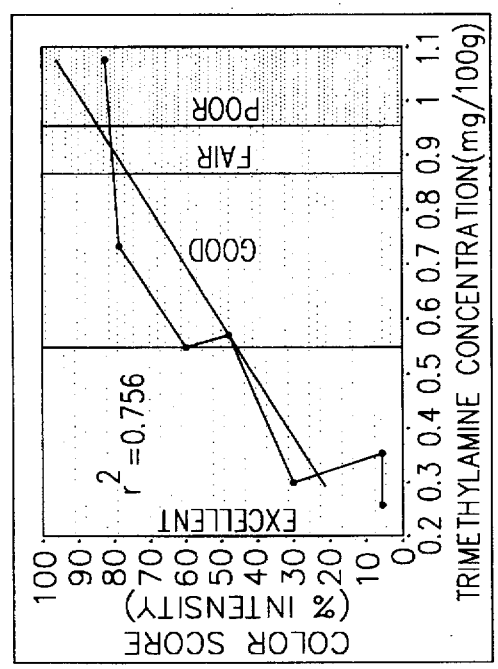

FIGS. 1 to 14 of the attached drawings show the relationship between color intensity and days of storage in ice, log. total aerobic plate counts, log. *Pseudomonas putrefaciens* plate counts, trimethylamine and sensory evaluation of codfish (FIGS. 1 to 5), catfish (FIGS. 6–9) and flounder (FIGS. 10–14). As indicated, for codfish, color was detected between 5 and 7 days of ice storage (FIG. 1). At this stage of detection, log. total aerobic plate count ranged from 6.3 to 7.0 (FIG. 2), whereas log. *Pseudomonas putrefaciens* count ranged from 4.0 to 5.0 (FIG. 3). This represented trimethylamine (TMA) levels of between 0.34 and 0.57 mg/100 g fish (FIG. 4). Sensory evaluation data (FIG. 5) using the "1" to "10" unstructured line scale indicate that using the present method of evaluation, the cod fish fillets can be assessed according to four categories of quality. These were premium quality (high)-representing up to 5 days of ice storage, (no color detected) with scores ranging from 1.0 to 2.9, high/medium (a stage of low color intensity), with scores ranging from 3.0 to 3.9, fair/medium (intermediate color intensity), and with scores >5.0 representing low/failure quality (intense red). Scores above 5.0 indicate that the sample is considered decomposed to the point of failure.

Figure 9:
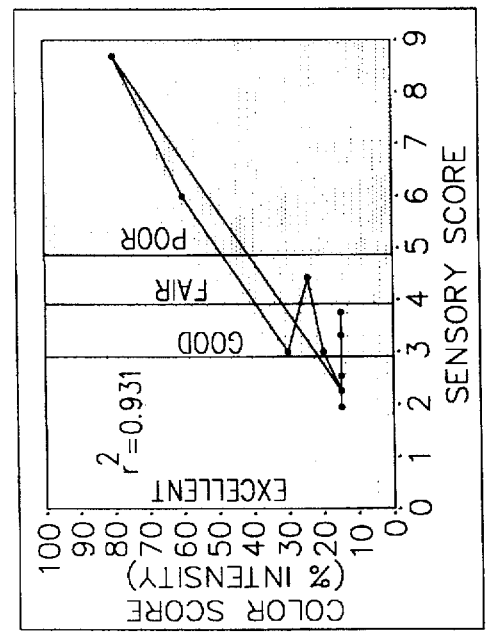
Figure 10:
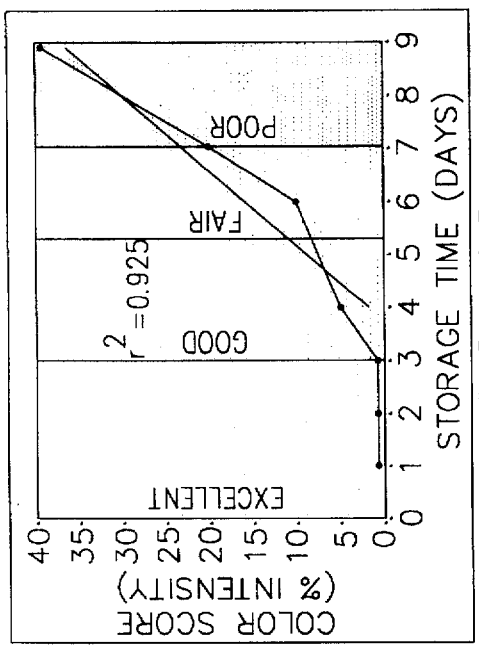
Figure 11:
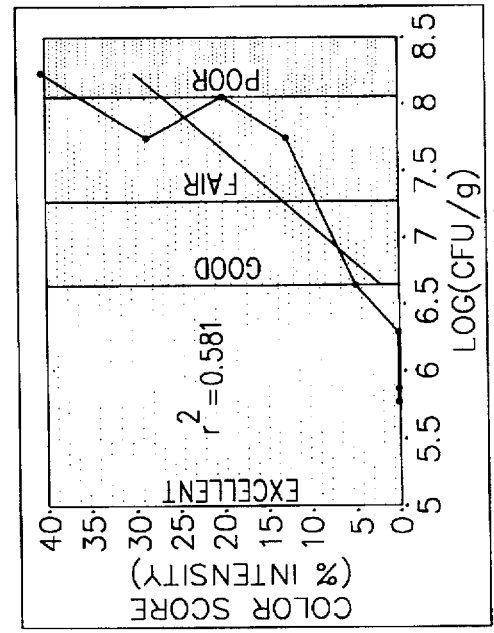

The relationship between other quality indicators of catfish quality and the present method are shown in FIGS. 6–9. According to FIG. 6, a significant appearance in color was detected between days 5 and 6 of ice storage. At this stage, log. total aerobic plate count ranged from 7.2 to 7.4 (FIG. 7), whereas log. *P. putrefaciens* count range from 6.0 to 6.2 (FIG. 8). Average sensory score from days 1–5 of ice storage ranged from 2.0 to 3.6, and for days 10–12 (the rejection period) ranged from 6.2 to 8.8 (FIG. 9).

Figure 12:
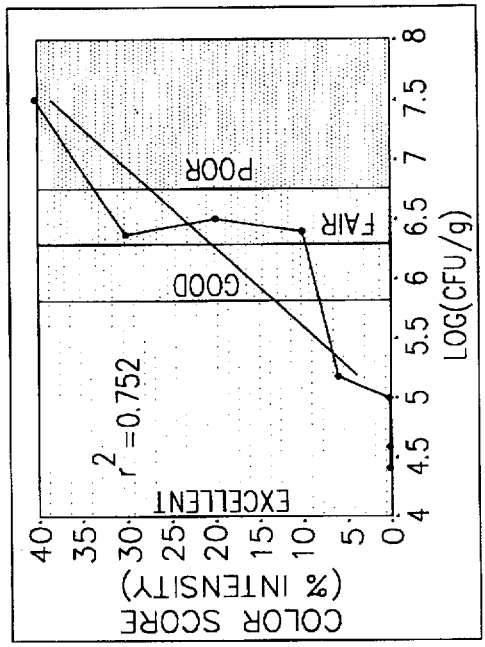
Figure 14:
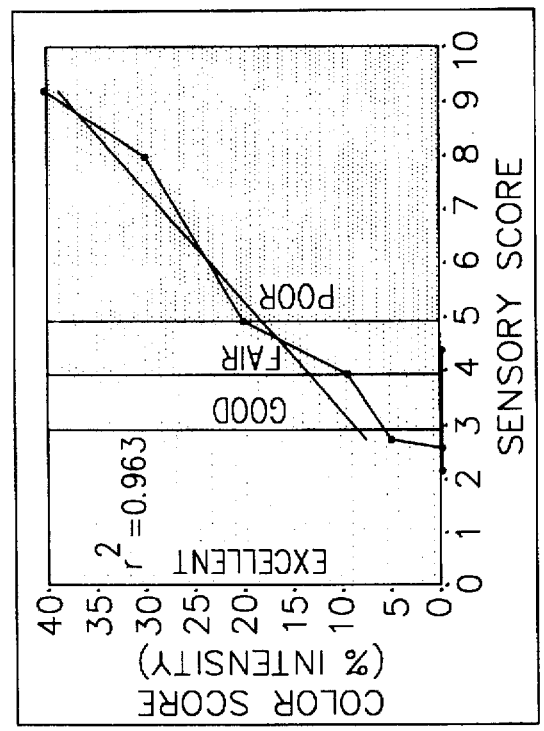
Figure 13:
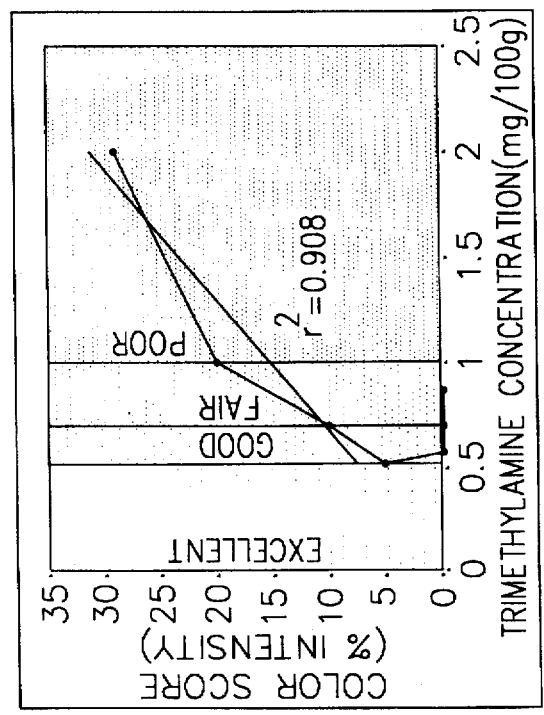

FIGS. 10–14 show the relationship between the various indicators of flounder quality and color score from the present method. In this study, color change was detected between days 3 and 4 of ice storage (FIG. 10), when log. total aerobic plate count (FIG. 11) ranged from 6.2 to 6.6, and log *P. putrefaciens* count ranged from 5.0 to 5.3 (FIG. 12). At this stage, trimethylamine level was 0.59 mg/100 g fish (FIG. 13). Sensory data (FIG. 14) also showed four stages of quality: High, which ranged from days 1–3 of ice storage; high-medium, days 4–5; medium, days 5–7; and low quality, days 7–10.

The present color test is a simple, rapid, reliable method for the assessment of finfish decomposition during ice storage. The method shows good correlation with other existing methods used to determine fish quality. Other advantages include: minimal sample preparation, ready to use sample reagents, room temperature testing, room temperature storage of reagents and easy disposal of waste materials.

The present method can be used in assessing critical control points for seafood quality. Although development was conducted using fish fillets stored in ice, the method could be adapted for use on whole and dressed fish stored in ice provided that proper sampling procedures are carried out, and the instructions provided in the kit followed closely.

The novel method of the present invention provides a rapid, accurate, in-situ system for evaluating the bacteria content of finfish as a measure of the degree of decomposition and value thereof since the present method yields results which correlate favorably with the results obtained using the traditional tests.

The reagents used in the present method include a water-soluble indicator reagent which undergoes a reduction reaction with the functioning electron transport system of viable bacteria present in the fish broth sample to deposit a water-insoluble red-colored reaction product within the bacterial cell.

The preferred indicator reagents are ionized 2,3,5-triphenyl tetrazolium halide salts, which react with bacteria commonly found in spoiled fish, such as *Pseudomonas putrefaciens*. The preferred salt is 2,3,5-triphenyl tetrazolium chloride.

The next important reagent, Reagent A, is a water-soluble surface active agent which produces lysis or rupture of the bacterial cells, releasing and solubilizing the formazan dye, and denaturing the fish protein to form a clear solution. The preferred surfactants are the anionic long chain alkyl alkaline earth metal sulfate surfactants or detergents such as sodium dodecyl sulfate.

The next important reagent, Reagent B, is an aliphatic alcohol having from 1 to 4 carbon atoms, preferably methanol, which functions to stabilize the color of the dissolved formazan dye, apparently by destroying any residual enzyme activity.

In the case of finfish having dark-colored or reddish flesh or muscle tissue, such as tuna fish, two additional reagents are required. The first, Reagent C, is a water-soluble bleaching agent which functions to oxidize and decolorize the red pigment present in the muscle flesh of tuna fish, such as hydrogen peroxide. The second additional reagent, Reagent D, is a defoaming agent which dissipates the foam generated by the bleaching reaction. Preferred reagents D are silicone defoamers such as dilute aqueous emulsions of dimethyl silicone.

It will be apparent to those skilled in the art in the light of the present disclosure that a wide variety of colorless, color-forming triphenyl tetrazolium dye salts are suitable for use as the indicator reagents in the present process, as well as a wide variety of other surface active agents, bleaching agents and defoaming agents.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A rapid, on-site method for indicating the degree of spoilage, if any, of finfish by quantifying the bacterial level present therein, comprising the steps of:

(a) cutting a small predetermined quantity of flesh from a representative finfish;

(b) kneading said flesh with a small predetermined quantity of a liquid bacterial nutrient broth for a brief period of time and then filtering off a small portion of the liquid extract;

(c) adding to the liquid extract a small predetermined quantity of an indicator reagent comprising a water-soluble ionized salt of a colorless tetrazolium dye which is reducible to form a water-insoluble colored formazan compound upon reaction with any bacteria present in the liquid, and allowing to stand for several minutes at room temperature;

(d) mixing a small amount of a surfactant with the liquid extract, (e) mixing a small amount of a lower aliphatic alcohol with the liquid extract, and (f) comparing the color of the liquid extract with a control color chart carrying colors of increasing intensity representative of various increasing concentrations of said colored formazan compound which is correlated to the concentration of said bacteria, whereby the absence of color indicates the presence of a low level of bacteria, if any, and the intensity of the color, if present, indicates the relative level of bacteria present and the degree of spoilage of the fish being examined.

2. The method according to claim 1 in which the ratio of fish flesh to liquid broth in step (b) is about 1 gram flesh per 1 ml broth.

3. The method according to claim 2 in which the amount of indicator reagent added in step (c) is about 1 ml per 5 ml of liquid extract.

4. The method according to claim 1 in which the surfactant mixed with the liquid extract in step (d) is an anionic surface active agent.

5. The method according to claim 4 in which the anionic surface active agent is a dilute aqueous solution of sodium dodecyl sulfate.

6. The method according to claim 5 in which the amount of surfactant mixed with the liquid extract in step (d) is between about 1 and 3 ml of the dilute aqueous solution of sodium dodecyl sulfate per 5 ml of the liquid extract.

7. The method according to claim 1 in which the aliphatic alcohol is methanol.

8. The method according to claim 7 in which the amount of alcohol mixed with the liquid extract in step (e) is about 1 ml per ml of the liquid extract.

9. The method according to claim 1 in which the indicator reagent comprises 2,3,5-triphenyl tetrazolium chloride.

10. The method according to claim 1 in which the fish flesh of step (a) is placed within a strainer bag and kneaded with the liquid nutrient broth in step (b) to facilitate filtering off of the liquid extract.

11. The method according to claim 1 for indicating the degree of decomposition, if any, of finfish having dark-colored flesh comprising the step of adding a dilute bleaching agent and a defoaming agent to the liquid extract of step (e), and allowing the mixture to react for several minutes prior to continuing with step (f).

12. The method according to claim 11 in which bleaching agent comprises 3% aqueous hydrogen peroxide.

13. The method according to claim 11 in which the defoaming agent comprises a dilute aqueous silicone emulsion.

* * * * *